US012566115B2

(12) United States Patent
Takimoto

(10) Patent No.: US 12,566,115 B2
(45) Date of Patent: Mar. 3, 2026

(54) ANALYZER AND ANALYSIS METHOD

(71) Applicant: Kioxia Corporation, Tokyo (JP)

(72) Inventor: Miki Takimoto, Yokkaichi Mie (JP)

(73) Assignee: KIOXIA CORPORATION, Tokyo (JP)

( * ) Notice: Subject to any disclaimer, the term of this patent is extended or adjusted under 35 U.S.C. 154(b) by 825 days.

(21) Appl. No.: 17/189,940

(22) Filed: Mar. 2, 2021

(65) Prior Publication Data

US 2022/0018743 A1 Jan. 20, 2022

(30) Foreign Application Priority Data

Jul. 15, 2020 (JP) ................................. 2020-121436

(51) Int. Cl.
| | |
|---|---|
| *G01N 1/38* | (2006.01) |
| *G01N 1/00* | (2006.01) |
| *G01N 1/02* | (2006.01) |
| *G01N 1/10* | (2006.01) |
| *G01N 33/202* | (2019.01) |
| *H01J 49/04* | (2006.01) |

(52) U.S. Cl.
CPC ................. *G01N 1/38* (2013.01); *G01N 1/02* (2013.01); *G01N 33/202* (2019.01); *H01J 49/0409* (2013.01); *H01J 49/0431* (2013.01); *G01N 2001/002* (2013.01); *G01N 2001/028* (2013.01); *G01N 2001/1031* (2013.01)

(58) Field of Classification Search
CPC ...... G01N 1/02; G01N 1/38; G01N 2001/002; G01N 33/202; H01J 49/0409; H01J 49/0431
USPC ...................................................... 73/864.91
See application file for complete search history.

(56) References Cited

U.S. PATENT DOCUMENTS

| | | | | |
|---|---|---|---|---|
| 4,990,459 A * | 2/1991 | Maeda | ................... | G01N 31/00 |
| | | | | 436/178 |
| 2002/0149775 A1* | 10/2002 | Mori | .................... | G01N 21/553 |
| | | | | 435/287.1 |
| 2016/0033390 A1* | 2/2016 | Coffin | ................ | G01N 21/0303 |
| | | | | 250/339.08 |

FOREIGN PATENT DOCUMENTS

| | | | | | |
|---|---|---|---|---|---|
| EP | 2899546 A1 * | 7/2015 | ........ | B01L 3/502723 |
| JP | 2944099 B2 * | 8/1999 | .......... | G01N 1/4055 |
| JP | 2003-017538 A | 1/2003 | | |
| JP | 2006228874 A * | 8/2006 | | |
| JP | 2008-132401 A | 6/2008 | | |
| JP | 2008-300605 A | 12/2008 | | |
| JP | 4740032 B2 * | 8/2011 | | |
| JP | 2011-232182 A | 11/2011 | | |
| KR | 20100077991 A * | 7/2010 | .......... | G01N 33/553 |
| WO | WO-2011140492 A2 * | 11/2011 | .......... | G01N 1/4055 |

* cited by examiner

*Primary Examiner* — Laura Martin
*Assistant Examiner* — Nashmiya S Fayyaz
(74) *Attorney, Agent, or Firm* — Foley & Lardner LLP

(57) ABSTRACT

An analysis system includes a stage that supports a sample. The analysis system includes a first supplier configured to provide a hydrophobic material on the sample, and surround an inspection region on the sample with the hydrophobic material. The analysis system includes a second supplier configured to provide an inspection liquid over the inspection region. The analysis system includes a collector configured to collect the inspection liquid. The analysis system includes an analyzer configured to analyze a component contained in the collected inspection liquid.

18 Claims, 8 Drawing Sheets

Figure 2:
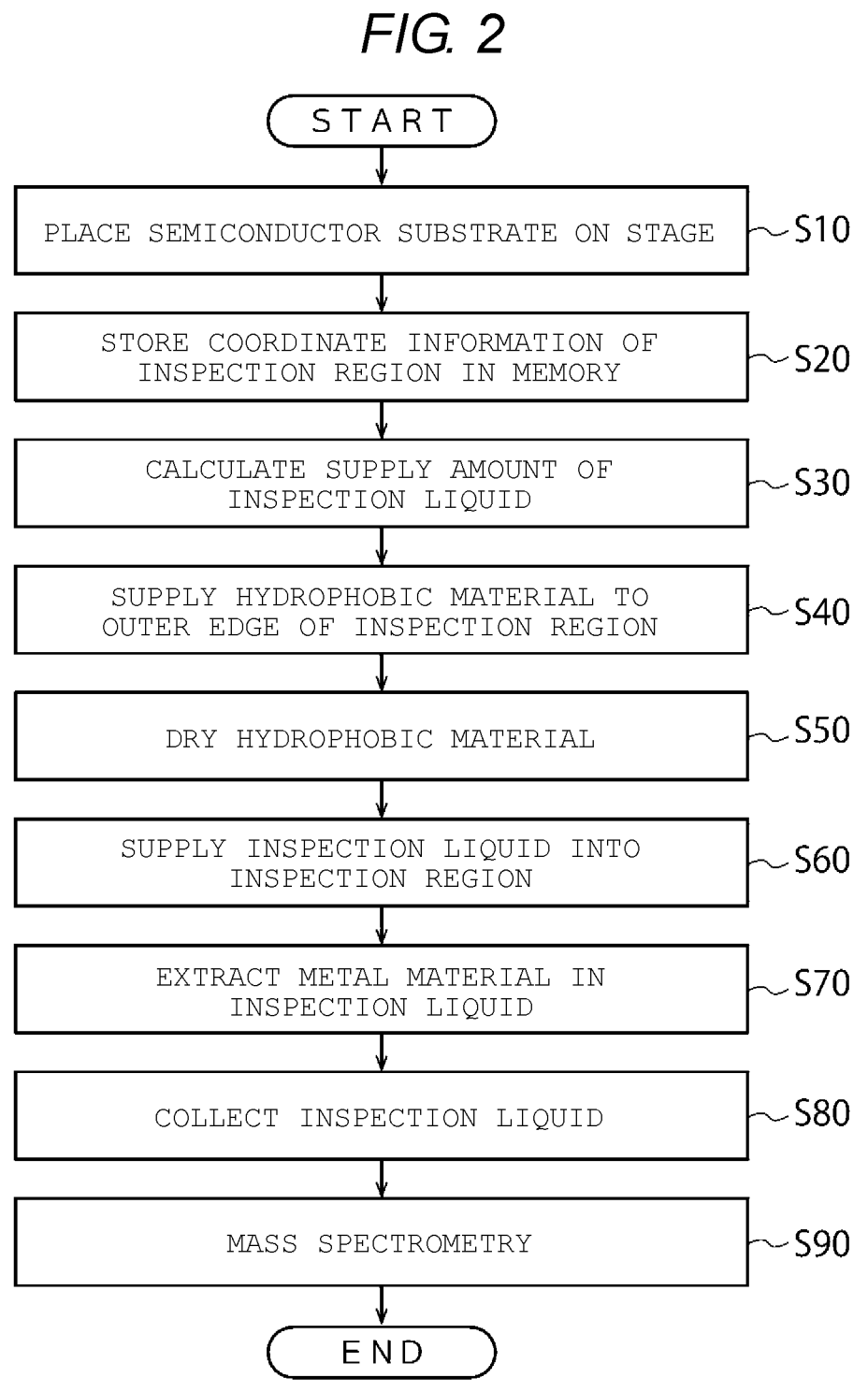

```
            ┌──────────────────┐
            │     START        │
            └──────────────────┘
                     │
                     ▼
   ┌─────────────────────────────────────────┐
   │  PLACE SEMICONDUCTOR SUBSTRATE ON STAGE  │─── S10
   └─────────────────────────────────────────┘
                     │
                     ▼
   ┌─────────────────────────────────────────┐
   │  STORE COORDINATE INFORMATION OF         │─── S20
   │  INSPECTION REGION IN MEMORY             │
   └─────────────────────────────────────────┘
                     │
                     ▼
   ┌─────────────────────────────────────────┐
   │  CALCULATE SUPPLY AMOUNT OF              │─── S30
   │  INSPECTION LIQUID                       │
   └─────────────────────────────────────────┘
                     │
                     ▼
   ┌─────────────────────────────────────────┐
   │  SUPPLY HYDROPHOBIC MATERIAL TO          │─── S40
   │  OUTER EDGE OF INSPECTION REGION         │
   └─────────────────────────────────────────┘
                     │
                     ▼
   ┌─────────────────────────────────────────┐
   │  DRY HYDROPHOBIC MATERIAL                │─── S50
   └─────────────────────────────────────────┘
                     │
                     ▼
   ┌─────────────────────────────────────────┐
   │  SUPPLY INSPECTION LIQUID INTO           │─── S60
   │  INSPECTION REGION                       │
   └─────────────────────────────────────────┘
                     │
                     ▼
   ┌─────────────────────────────────────────┐
   │  EXTRACT METAL MATERIAL IN               │─── S70
   │  INSPECTION LIQUID                       │
   └─────────────────────────────────────────┘
                     │
                     ▼
   ┌─────────────────────────────────────────┐
   │  COLLECT INSPECTION LIQUID               │─── S80
   └─────────────────────────────────────────┘
                     │
                     ▼
   ┌─────────────────────────────────────────┐
   │  MASS SPECTROMETRY                       │─── S90
   └─────────────────────────────────────────┘
                     │
                     ▼
            ┌──────────────────┐
            │      END         │
            └──────────────────┘
```

ANALYZER AND ANALYSIS METHOD

CROSS-REFERENCE TO RELATED APPLICATION

This application is based upon and claims the benefit of priority from Japanese Patent Application No. 2020-121436, filed Jul. 15, 2020, the entire contents of which are incorporated herein by reference.

FIELD

Embodiments described herein relate generally to an analyzer and an analysis method.

BACKGROUND

When a semiconductor device is contaminated with undesired metal, such metal contamination caused leads to deterioration in performance of the semiconductor device or a defect in a manufacturing process thereof. A metal analyzer such as an inductively coupled plasma-mass spectrometry (ICP-MS) maybe used in order to specify a cause of the defect and a location thereof due to such metal contamination. The metal analyzer collects a liquid after wiping or scanning the semiconductor device by the liquid, and performs mass spectrometry on a metal component contained in the collected liquid.

However, when the liquid is wiped to collect the metal contamination, it is required to immerse a wiping material in the liquid such that collection work is complicated. Other impurities are easy to be mixed into the wiping material and wiping work, thereby hindering accurate metal analysis. On the other hand, when scanning a surface of the semiconductor device with a liquid stored in a nozzle, it is not possible to scan a region smaller than a size of the nozzle. Conversely, when the size of the nozzle is made significantly small, there is a problem that it takes a long time to scan a wide range.

DESCRIPTION OF THE DRAWINGS

FIG. 2 is a flowchart illustrating an example of an analysis method using the metal analyzer according to the first embodiment;

DETAILED DESCRIPTION

Embodiments provide an analyzer and an analysis method in which an inspection liquid can be easily supplied and collected to and from a desired inspection region, and mass spectrometry can be accurately performed on a component contained in the inspection liquid.

In general, according to one embodiment, an analysis system includes a stage that supports a sample. The analysis system includes a first supplier configured to provide a hydrophobic material on the sample, and surround an inspection region on the sample with the hydrophobic material. The analysis system includes a second supplier configured to provide an inspection liquid over the inspection region. The analysis system includes a collector configured to collect the inspection liquid. The analysis system includes an analyzer configured to analyze a component contained in the collected inspection liquid.

Hereinafter, embodiments according to the present disclosure will be described with reference to the drawings. The embodiments are not intended to limit the present disclosure. The drawings are schematic or conceptual, and a ratio of each part is not necessarily the same as that of the actual one. In the specification and the drawings, the same elements as those described earlier in above-described drawings will be denoted by the same reference signs, and detailed description thereof will be appropriately omitted.

First Embodiment

Figure 1:
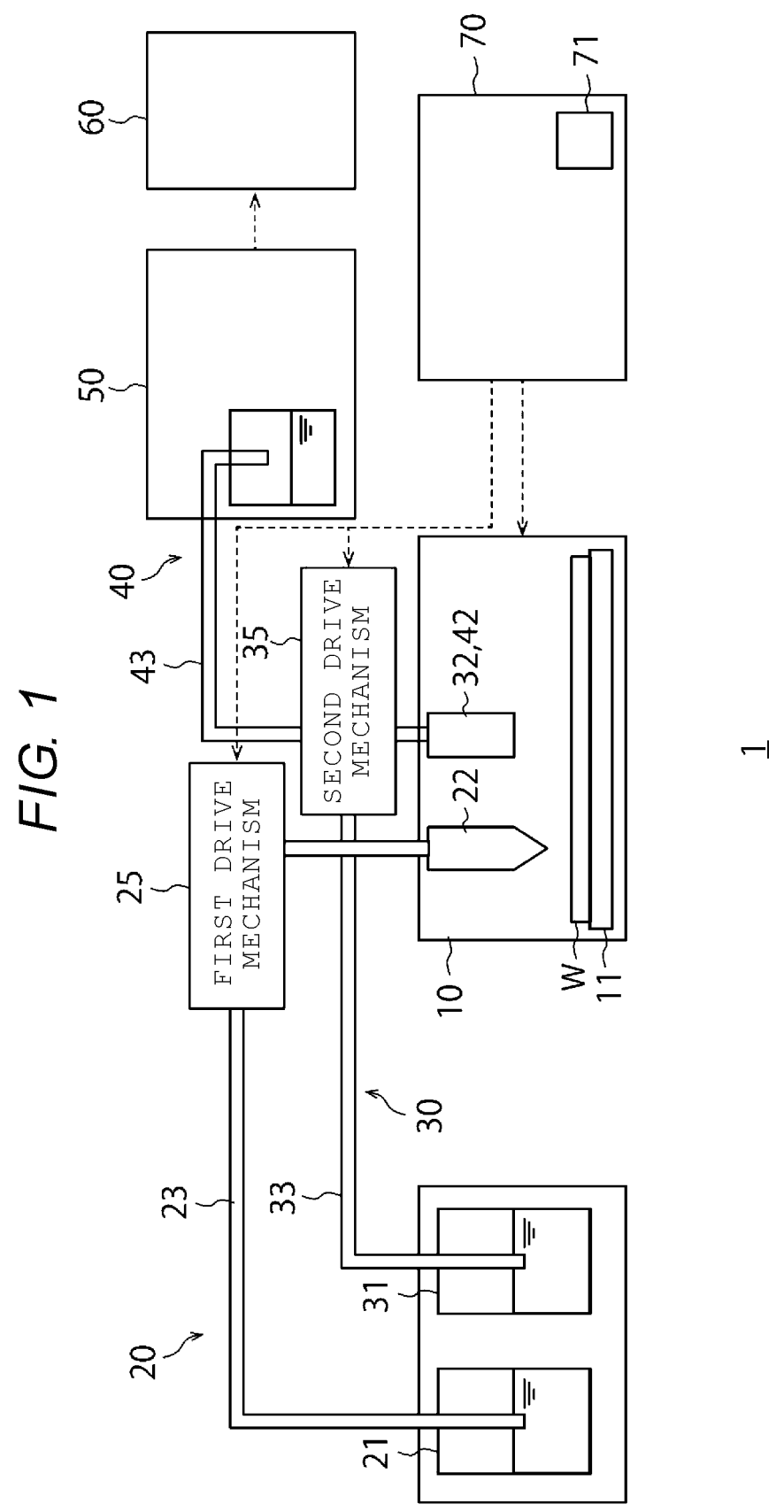
FIG. 1 is a block diagram illustrating a configuration example of a metal analyzer according to a first embodiment.

FIG. 1 is a block diagram illustrating a configuration example of a metal analyzer 1 according to a first embodiment. For example, the metal analyzer 1 may be an analyzer such as an ICP-MS.

The metal analyzer 1 includes a chamber 10, a stage 11, a hydrophobic material supply unit (supplier) 20, a hydrophobic material storage unit (device) 21, a nozzle 22 for supplying a hydrophobic material, an inspection liquid supply unit (supplier) 30, an inspection liquid storage unit (device) 31, a nozzle 32 for supplying the inspection liquid, a collection unit (collector) 40, a nozzle 42 for collection, an inspection liquid sampler 50, an analysis unit (analyzer) 60, a controller 70, and a memory 71.

The chamber 10 can house a semiconductor substrate W as a sample, and supplies an inspection liquid on the semiconductor substrate W and collect the inspection liquid. An inside of the chamber 10 may be decompressed, or may be under normal pressure. Temperature inside the chamber 10 may be at room temperature. The stage 11 is arranged in the chamber 10, and is configured so that the semiconductor substrate W can be placed thereon.

The hydrophobic material supply unit 20 can supply, apply or otherwise provide the hydrophobic material on the semiconductor substrate W to provide hydrophobicity, which can define a region surrounded by the hydrophobic material as an inspection region. The hydrophobic material is not particularly limited, and, for example, is a liquid containing 1-bromopropane ($CH_3CH_2CH_2Br$) of about 60.5%, butyl rubber (isobutylene-isoprene rubber) of about 30%, and petroleum solvent of about 9.5%. Hydrophobicity of the hydrophobic material can be improved by drying the hydrophobic material after applying the hydrophobic material. Therefore, it is desirable that the hydrophobic material is dried at room temperature for a short time. Since the inspection liquid is acidic, it is desirable that the inspection liquid is an acid-resistant material.

The hydrophobic material supply unit 20 includes the hydrophobic material storage unit 21, the nozzle 22, and a pipe 23. The hydrophobic material storage unit 21 stores the hydrophobic material. The nozzle 22 is provided in the chamber 10, and supplies the hydrophobic material to the semiconductor substrate W placed on the stage 11. A tip end of the nozzle 22 is a sharp hollow tube, and can continuously discharge the hydrophobic material. The pipe 23 communicates from the hydrophobic material storage unit 21 to the nozzle 22, and sends the hydrophobic material from the hydrophobic material storage unit 21 to the nozzle 22.

The inspection liquid supply unit 30 supplies the inspection liquid into the inspection region surrounded by the hydrophobic material on the semiconductor substrate W. Accordingly, the inspection liquid can retain in the inspection region. The inspection liquid is not particularly limited, and is a liquid that dissolves a substance (for example, metal) which becomes a target to be subjected to mass spectrometry. The inspection liquid may include, for example, at least one of a liquid containing HF and $H_2O$, a liquid containing HF and $H_2O_2$, a liquid containing HF, HCl, and $H_2O_2$, or a liquid containing HF, $HNO_3$, and HCl. The substance which becomes the target to be subjected to the mass spectrometry may be any element as long as the substance includes metal.

The inspection liquid supply unit 30 includes the inspection liquid storage unit 31, the nozzle 32, and a pipe 33. The inspection liquid storage unit 31 stores the inspection liquid. The nozzle 32 is provided in the chamber 10, and supplies the inspection liquid to the semiconductor substrate W placed on the stage 11. The nozzle 32 is a hollow tube, and can continuously discharge the inspection liquid. The pipe 33 communicates from the inspection liquid storage unit 31 to the nozzle 32, and sends the inspection liquid from the inspection liquid storage unit 31 to the nozzle 32.

The collection unit 40 includes the nozzle 42, a pipe 43, and the inspection liquid sampler 50. The nozzle 42 is provided in the chamber 10, and suctions the inspection liquid staying in the inspection region of the semiconductor substrate W. The nozzle 42 is integrated with the nozzle 32, and moves together with the nozzle 32. The nozzle 42 is a hollow tube, and can suction and collect the inspection liquid. The hollow tube of the nozzle 42 and the hollow tube of the nozzle 32 may be individually provided, and may be provided in common. The pipe 43 communicates between the nozzle 42 and the inspection liquid sampler 50, and sends the inspection liquid collected from the inspection region to the inspection liquid sampler 50. The inspection liquid stays in the inspection region, and melts a metal material which becomes a target to be analyzed. The inspection liquid sampler 50 stores the inspection liquid to be used for the mass spectrometry. The analysis unit 60 performs the mass spectrometry on the inspection liquid collected from the inspection region.

For example, the analysis unit 60 performs the mass spectrometry on an amount of a metal component contained in the inspection liquid by the ICP-MS. When the inspection region of the semiconductor substrate W is contaminated with metal (for example, sodium), the inspection liquid melts and takes in the contaminated metal. Next, the analysis unit 60 can specify an element of the contaminated metal and an amount thereof by performing the mass spectrometry on the metal component contained in the collected inspection liquid.

A first drive mechanism 25 moves the nozzle 22 of the hydrophobic material supply unit 20 under the control of the controller 70. For example, the first drive mechanism 25 drives the hydrophobic material supply unit 20 so that the tip end of the nozzle 22 surrounds the inspection region with the hydrophobic material while supplying the hydrophobic material from the nozzle 22 of the hydrophobic material supply unit 20. Accordingly, the first drive mechanism 25 can supply the hydrophobic material along an outer edge of the inspection region, and surround the inspection region with the hydrophobic material. When the hydrophobic material is dried, the outer edge of the inspection region is hydrophobized.

A second drive mechanism 35 moves the nozzle 32 of the inspection liquid supply unit 30 under the control of the controller 70. For example, the second drive mechanism 35 moves the nozzle 32 of the inspection liquid supply unit 30 to an upper part of the inspection region, and supplies the inspection liquid from the nozzle 32 into the inspection region. Here, the outer edge of the inspection region is hydrophobized by the hydrophobic material. Therefore, the inspection liquid can stay in the inspection region. A supply amount of the inspection liquid is required to be changed depending on an area of the inspection region. The reason of changing the supply amount thereof is that even though the outer edge of the inspection region is hydrophobized, the inspection liquid may overflow from the inspection region when the amount of the inspection liquid is too large. The area of the inspection region can be calculated from a distance applied with the hydrophobic material, that is, a moving distance of the nozzle 22, and an outer shape of the inspection region. By appropriately changing the amount of the inspection liquid according to the area of the inspection region, an appropriate amount of the inspection liquid can be supplied into the inspection region. Accordingly, the analysis unit 60 can accurately perform the mass spectrometry on the component melted in the inspection liquid.

In the embodiment, the nozzle 42 of the collection unit 40 may be configured to be integrated with the nozzle 32 of the inspection liquid supply unit 30, or one hollow tube may be shared as a common nozzle. Therefore, the nozzle 42 can be driven by the second drive mechanism 35 together with the nozzle 32. That is, the second drive mechanism 35 can drive the collection unit 40, thereby making it possible to move the nozzle 42 above the inspection region.

The controller 70 controls not only the first and second drive mechanisms but also each configuration of the metal analyzer 1 such as the stage 11. For example, the controller 70 controls the first and second drive mechanisms 25 and 35 based upon coordinate information of the semiconductor substrate W and coordinate information of the inspection region. The controller 70 controls the hydrophobic material supply unit 20, the inspection liquid supply unit 30, and the collection unit 40, and executes a supply operation of the inspection liquid and a collection operation thereof, based upon a sequence and a program stored in the memory 71.

The memory 71 stores the coordinate information of the semiconductor substrate W placed on the stage 11, coordinate information on a surface of the semiconductor substrate W, a sequence indicating an operation of the nozzles 22, 32, and 42 at the time of supplying or collecting the hydrophobic material and the inspection liquid, a condition such as atmospheric pressure, temperature, and humidity in the chamber 10, and a condition such as temperature of the stage 11. The memory 71 also stores a program for controlling the metal analyzer 1.

Next, an analysis method using the metal analyzer 1 according to the embodiment will be described.

FIG. 2 is a flowchart illustrating an example of an analysis method using the metal analyzer 1 according to the first embodiment.

First, the semiconductor substrate W is placed on the stage 11 in the chamber 10 (S10).

Next, the coordinate information of the inspection region is stored in the memory 71 in order to specify the inspection region on the surface of the semiconductor substrate W (S20). For example, the coordinate information of the inspection region may be fetched from an external computer. The inspection region is assumed to be, for example, a region of a defective location of 50 mm×50 mm on the surface of the semiconductor substrate W. The inspection region may be a part or the whole of a defective semiconductor chip. When the inspection region is the whole semiconductor chip, the hydrophobic material is supplied to a dicing line of an outer edge of the semiconductor chip. The inspection region may be one location or a plurality of locations.

The inspection region may be set to a predetermined shape and a predetermined area. The predetermined shape may be, for example, a square, a rectangle, a circle, an ellipse, a triangle, and a polygon. A method for moving the hydrophobic material supply unit 20 is facilitated by setting the shape and area of the inspection region before the hydrophobic material supply unit 20 is moved. The amount of the inspection liquid supplied from the inspection liquid supply unit 30 can be maintained at an approximately constant amount by setting the area of the inspection region before the inspection liquid is supplied therefrom. Accordingly, a movement sequence of the hydrophobic material supply unit 20 and a supply sequence of the inspection liquid of the inspection liquid supply unit 30 are facilitated.

When the area of the inspection region is almost constant, the amount of the inspection liquid supplied to the inspection region can be set before the inspection liquid is supplied thereto, and is almost constant. The preset supply amount of the inspection liquid may be registered in the memory 71. On the other hand, when the area of the inspection region is not constant, the controller 70 may calculate the area of the inspection region from a coordinate of the inspection region, and may calculate the supply amount of the inspection liquid corresponding to the area thereof (S30). The supply amount of the inspection liquid is set to such a degree that the inspection liquid is sufficiently distributed over the inspection region and does not overflow from the inspection region. For example, the supply amount of the inspection liquid may be calculated as a predetermined amount (for example, 0.5 ml/cm$^2$) with respect to a unit area of the inspection region.

Next, the hydrophobic material supply unit 20 is driven according to the coordinate information of the inspection region, the nozzle 22 is moved along the outer edge of the inspection region, and the hydrophobic material is supplied to the outer edge of the inspection region (S40). Accordingly, the inspection region is surrounded by the hydrophobic material, and the inspection region is defined. In various embodiments, the hydrophobic material is supplied to continuously surround the outer edge of the inspection region so that the inspection liquid does not spread outside from the inspection region in a subsequent step. A speed at which the nozzle 22 moves on the surface of the semiconductor substrate W is, for example, about 30 mm/sec.

Next, the hydrophobic material is dried (S50). The hydrophobic material may be naturally dried in the atmosphere in the chamber 10, or maybe dried by heating. Alternatively, the hydrophobic material may be dried by decompressing the inside of the chamber 10. The drying time of the hydrophobic material is, for example, about 1 min.

Next, the inspection liquid supply unit 30 is driven according to the coordinate information of the inspection region, the nozzle 32 is moved above the inspection region, and the inspection liquid is supplied into the inspection region (S60). Accordingly, the inspection liquid is supplied to the inspection region. The inspection liquid is supplied thereinto with a predetermined amount or the amount calculated in step S30 so that the inspection liquid sufficiently spreads over the inspection region and does not overflow from the inspection region. The inspection liquid is not supplied to an outside of the inspection region. When a plurality of inspection regions are set, the inspection liquid supply unit 30 supplies the inspection liquid to each of the plurality of inspection regions.

Next, the inspection liquid stays in the inspection region and is left therein as it is, and a metal material which is a target to be analyzed is dissolved in the inspection liquid and extracted (S70). The inspection liquid dissolves and contains the metal material.

Next, the collection unit 40 is driven according to the coordinate information of the inspection region, the nozzle 42 is moved above the inspection region, and the inspection liquid is collected by the nozzle 42 (S80). When the nozzle 42 is integrated with the nozzle 32, after the inspection liquid supply unit 30 supplies the inspection liquid to a certain inspection region, the second drive mechanism 35 may move the nozzle 42 together with the nozzle 32 to an original inspection region. The inspection liquid sampler 50 stores the inspection liquid collected by the collection unit 40.

After collecting the inspection liquid sampler 50, the analysis unit 60 performs mass spectrometry on the inspection liquid (S90). Since a well-known ICP-MS method may be used as the mass spectrometry itself, the description thereof will be omitted here.

As described above, the metal analyzer 1 according to the embodiment supplies the hydrophobic material to the outer edge of the inspection region of the semiconductor substrate W, thereby allowing the outer edge of the inspection region to be hydrophobized. Accordingly, the outer edge of the inspection region is hydrophobized, such that the inspection liquid can easily stay in the inspection region. When the inspection liquid is water-based liquid, the hydrophobic material may be used, but when the inspection liquid is a liquid other than water-based liquid, a hydrophobic material having hydrophobicity with respect to the liquid is used.

By allowing the inspection liquid to stay in the inspection region, the hydrophobic material easily takes in a contaminant (for example, metal material) existing in the inspection region. The hydrophobic material does not leak to the outside of the inspection region, and the hydrophobic material can accurately take in the contaminant in the inspection region. As a result, the mass spectrometry can be accurately performed.

Since one or a plurality of inspection regions can be defined on the semiconductor substrate W, it is not required to scan the whole semiconductor substrate W, and the inspection liquid can be supplied and collected in a short time.

Even when the inspection region is smaller than an opening area of the nozzle, the inspection liquid can stay in the inspection region when the inspection region can be surrounded by the hydrophobic material. Therefore, since it is not required to collect the inspection liquid by wiping or to dice the semiconductor substrate W into individual pieces, complicated work is not required, and a risk of allowing other impurities to be mixed into the inspection liquid is low.

In order to ensure quantitative properties of an interference element and a high-spectrum element, in a related art, it is required to select a measurement condition and to perform correction calculation using an internal standard element. Easy surface analysis can be performed by the present disclosure.

Figure 3A:
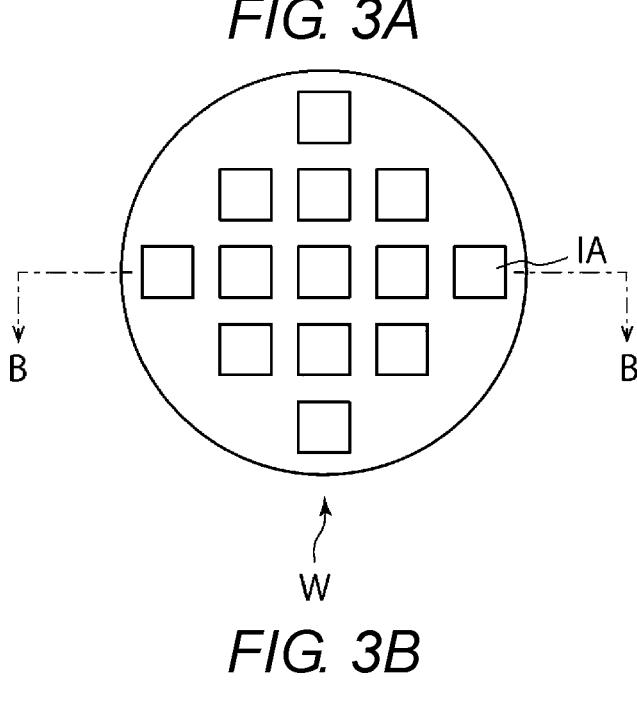
FIG. 3A is a plan view illustrating an inspection region on a semiconductor substrate.
Figure 3B:
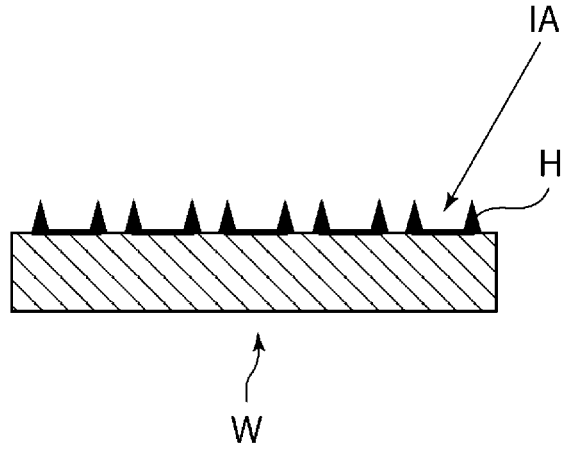
FIG. 3B is a cross-sectional view taken along the line B-B of FIG. 3A.

For example, FIG. 3A is a plan view illustrating an inspection region IA on the semiconductor substrate W. FIG. 3B is a cross-sectional view taken along the line B-B of FIG. 3A. For example, thirteen inspection regions IA are set on the semiconductor substrate W. Each inspection region IA is, for example, an approximately square region of 50 mm×50 mm. The inspection region IA is surrounded by a hydrophobic material H on the surface of the semiconductor substrate W. For example, the inspection region IA may be considered as the whole semiconductor chip or a part thereof.

When the inspection region IA is scanned with the inspection liquid and then the inspection liquid is collected without hydrophobization of the inspection region IA, for example, it takes about 0.5 min to separate and purify the inspection liquid by a predetermined amount. For example, it takes about 1 min to scan one inspection region IA with the inspection liquid. For example, it takes about 20 seconds to collect the inspection liquid. For example, it takes about 10 seconds to collect the inspection liquid by suctioning up the collected inspection liquid up to a collection container. Such a series of inspection liquid collection operations takes about 2 min. The inspection liquid collection operation is performed in each inspection region IA. Accordingly, it takes about 26 min to collect the inspection liquid from the 13 inspection regions IA. Even though two nozzles for discharging and collecting the inspection liquid are provided, it takes about 13 min to collect the inspection liquid from all the inspection regions IA.

Figure 4:
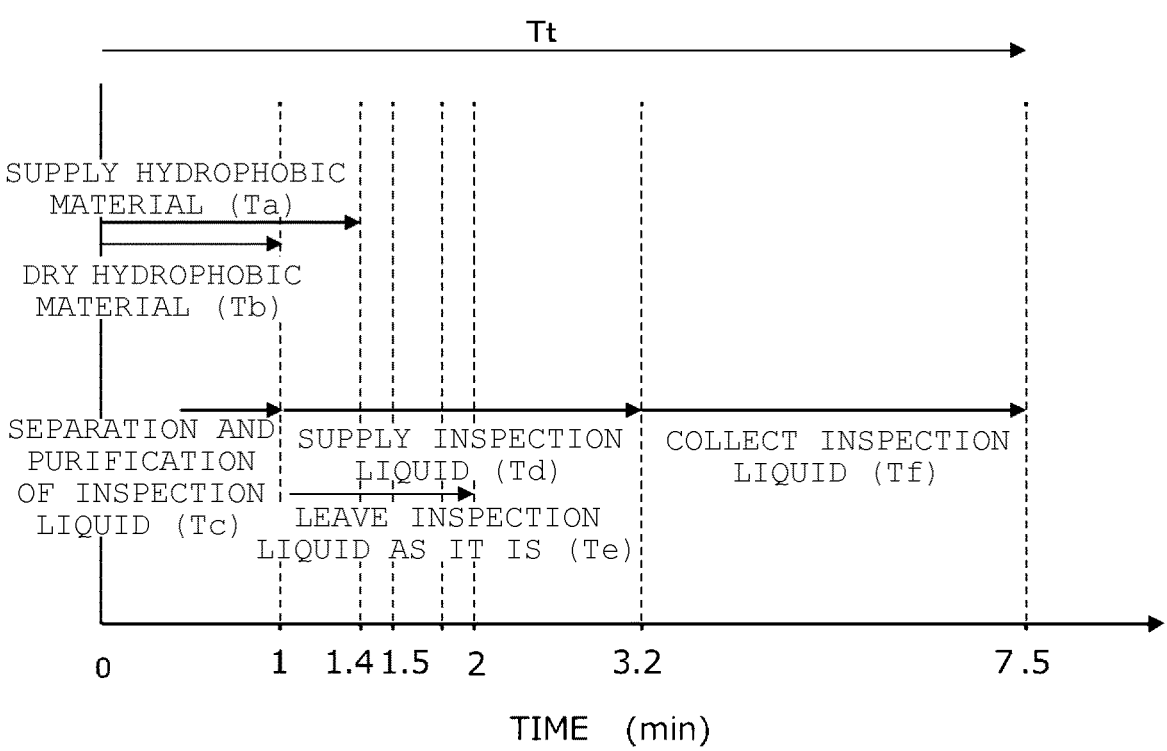
FIG. 4 is a graph illustrating time required for performing the analysis method according to the present embodiment.

FIG. 4 is a graph illustrating the time required for performing the analysis method according to the embodiment. As illustrated in FIG. 4, in the metal analyzer 1 according to the embodiment, it takes, for example, about 1.4 min (Ta) to scan the outer edge of the inspection region IA with the hydrophobic material. It is assumed that a speed at which the nozzle 22 moves on the surface of the semiconductor substrate W is, for example, about 30 mm/sec.

The drying time of the hydrophobic material is, for example, about 1 min (Tb). However, since the hydrophobic material begins to dry immediately after being supplied, the supply of the inspection liquid can start before the hydrophobic material is supplied to the outer edges of all the inspection regions IA. That is, drying time Tb of the hydrophobic material can almost overlap with supply time Ta of the hydrophobic material. The separation and purification of the inspection liquid takes, for example, about 0.5 min (Tc), and can be performed independently of the supply and drying of the hydrophobic material. Therefore, the inspection liquid supply unit 30 can separate and purify the inspection liquid during the supply time Ta and/or the drying time Tb of the hydrophobic material, thereby making it possible to prepare for the supply of the inspection liquid. That is, the separation and purification time Tc of the inspection liquid can almost overlap with the supply time Ta of the hydrophobic material or the drying time Tb of the hydrophobic material.

After the separation and purification of the inspection liquid, the inspection liquid supply unit 30 supplies the inspection liquid to the inspection region IA where the hydrophobic material is dried. It takes, for example, about 2.2 min (10 sec×13) (Td) to supply the inspection liquid to all the inspection regions IA. It is assumed that the time required for supplying the inspection liquid to one inspection region IA is 10 sec.

Time for leaving the inspection liquid as it is (metal extraction time) Te is, for example, about 1 min. Since leaving the inspection liquid as it is starts simultaneously with execution of the supply of the inspection liquid, the time for leaving the inspection liquid as it is Te almost overlaps with the supply time Td of the inspection liquid.

After the lapse of the time for leaving the inspection liquid as it is Te, the collection of the inspection liquid starts. It takes, for example, about 4.3 min (20 sec×13) (Tf) to collect the inspection liquid in all the inspection regions IA. It is assumed that the time for collecting and sending the inspection liquid in one inspection region IA from the inspection region IA to the inspection liquid sampler 50 is 20 sec.

When the nozzle 42 of the collection unit 40 is integrated with the nozzle 32 of the inspection liquid supply unit 30, the collection of the inspection liquid is executed after the inspection liquid is supplied.

Total time Tt from the start of supplying the hydrophobic material to the outer edge of the inspection region IA to the end of the collection of the inspection liquid in the inspection region IA is, for example, about 7.5 min.

Figure 5:
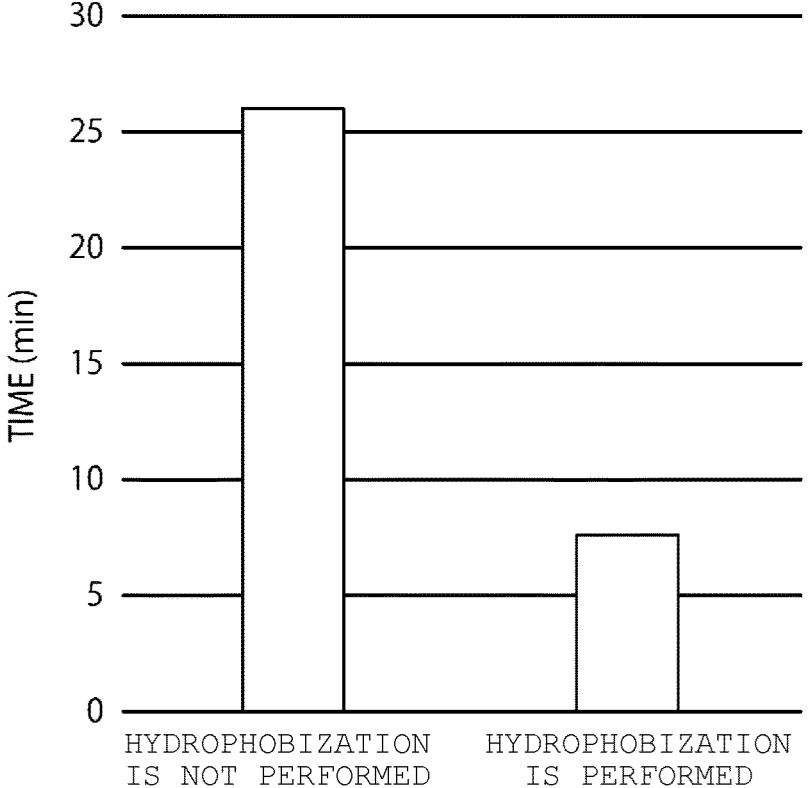
FIG. 5 is a graph illustrating collection time of an inspection liquid when an outer edge of the inspection region is not hydrophobized and collection time of the inspection liquid when the outer edge of the inspection region is hydrophobized.

FIG. 5 is a graph illustrating collection time of the inspection liquid when the outer edge of the inspection region IA is not hydrophobized and collection time of the inspection liquid when the outer edge of the inspection region IA is hydrophobized. As described above, the metal analyzer 1 according to the embodiment can collect the inspection liquid in less than one-third of the time in comparison with the case in which the inspection region IA is scanned with the inspection liquid and then the inspection liquid is collected without the hydrophobization of the inspection region IA (about 26 min). As described above, the metal analyzer 1 and the analysis method according to the embodiment can shorten the collection time of the inspection liquid.

In the embodiment, the hydrophobic material and the inspection liquid can be automatically supplied, and the inspection liquid can be automatically collected. Therefore, in the embodiment, an impurity is hardly mixed into the collected inspection liquid in comparison with a collection method using a wiping material.

(Modification)

Figure 6:
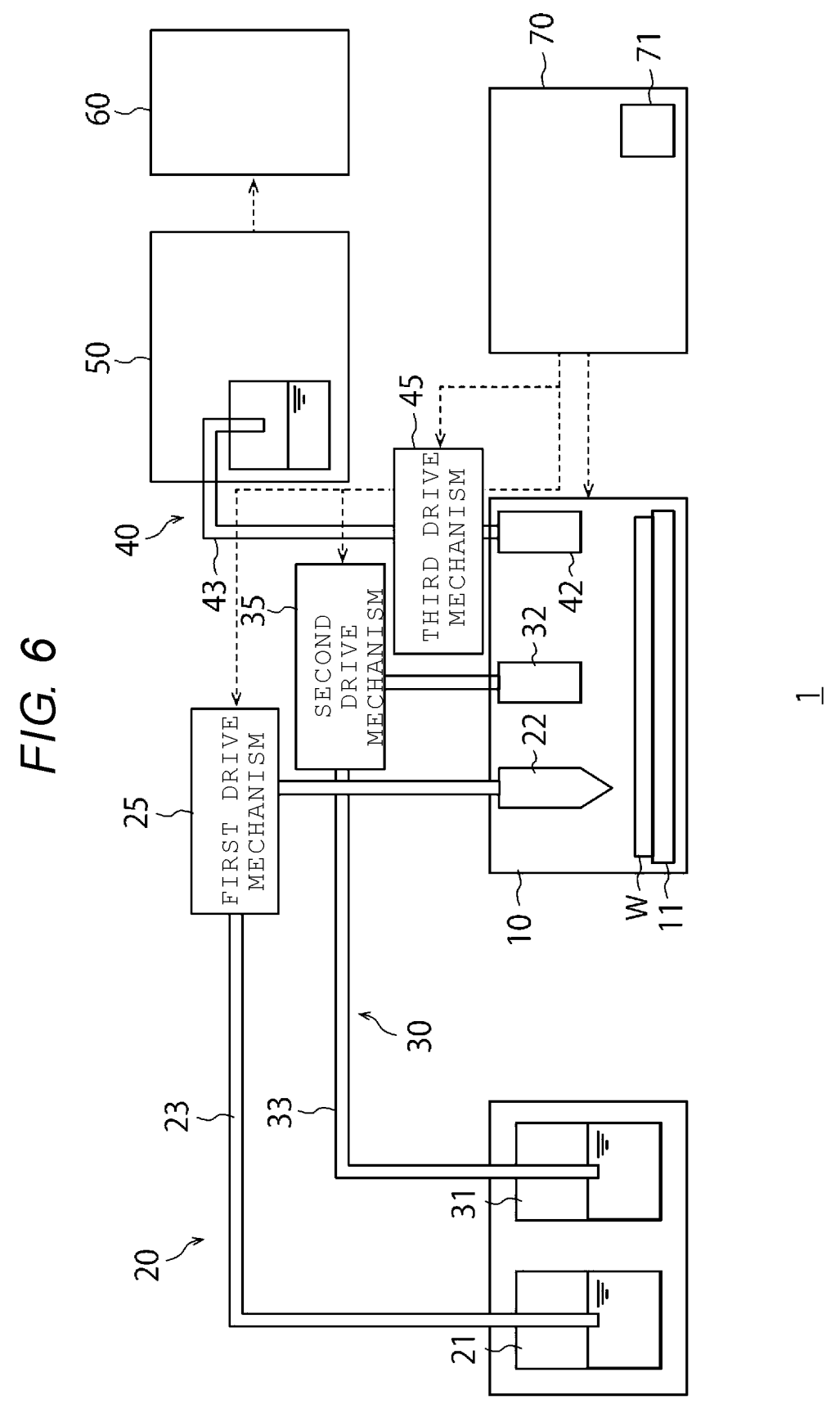
FIG. 6 is a block diagram illustrating a configuration example of a metal analyzer according to a modification of the first embodiment.

FIG. 6 is a block diagram illustrating a configuration example of the metal analyzer 1 according to a modification of the first embodiment. In the first embodiment, the nozzle 32 of the inspection liquid supply unit 30 and the nozzle 42 of the collection unit 40 are configured to be integrated with each other. However, in the modification, the nozzle 32 and the nozzle 42 are configured to be individually provided, and to be independently controllable. Here, the metal analyzer 1 further includes a third drive mechanism 45 that drives the collection unit 40. The third drive mechanism 45 can move the nozzle 42. On the other hand, the second drive mechanism 35 drives only the inspection liquid supply unit 30 to move the nozzle 32.

As such, the nozzle 32 of the inspection liquid supply unit 30 and the nozzle 42 of the collection unit 40 are individually controlled, thereby making it possible to perform the supply operation of the inspection liquid and the collection operation of the supplied inspection liquid in parallel (overlapping). Here, since the supply time Td of the inspection liquid and the collection time Tf of the inspection liquid in FIG. 4 can overlap with each other, the total time Tt from the start of supplying the hydrophobic material to the end of the collection of the inspection liquid can be further shortened.
(Modification of Nozzle)

Figures 7A, 7B, 7C:
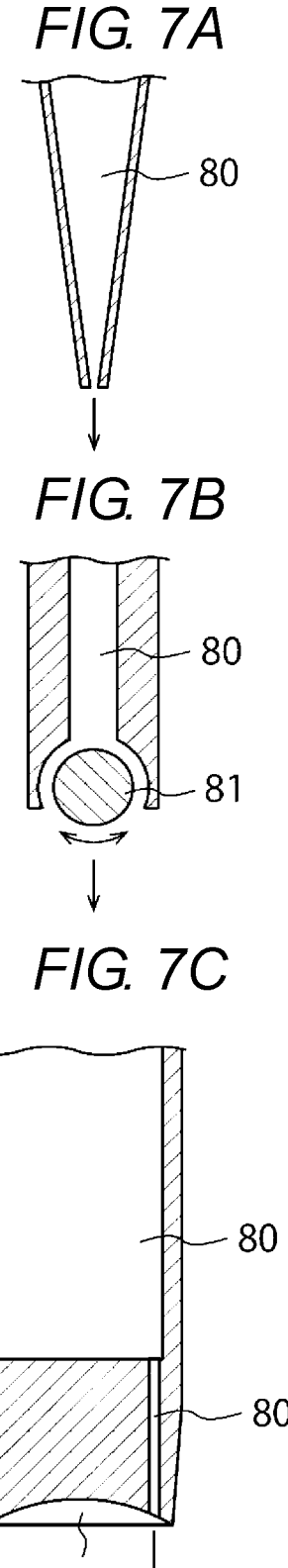
FIG. 7A is a cross-sectional view illustrating a modification of a nozzle.
FIG. 7B is a cross-sectional view illustrating a modification of the nozzle.
FIG. 7C is a cross-sectional view illustrating a modification of the nozzle.

FIGS. 7A to 7C are cross-sectional views illustrating modifications of the nozzles 22, 32, and 42. The nozzles 22, 32, and 42 may have any one of structures illustrated in FIGS. 7A to 7C.

The nozzle illustrated in FIG. 7A has an approximately conical shape, and a hollow tube 80 narrows toward a tip end of the nozzle. The tip end part is opened to communicate with the hollow tube 80. An opening diameter of the nozzle tip end is, for example, about 2 mm. A length of the nozzle is, for example, about 4 mm. The hydrophobic material or the inspection liquid is discharged in an arrow direction. Alternatively, the inspection liquid is collected in a direction opposite to the arrow direction.

The nozzle illustrated in FIG. 7B is a ballpoint pen type. A ball 81 is rotatably provided at the tip end of the nozzle, and the hydrophobic material or the inspection liquid is discharged from the hollow tube 80 according to the rotation of the ball 81. The hydrophobic material or the inspection liquid is stored in the hollow tube 80 when the ball 81 does not rotate. On the other hand, the nozzle 42 of the collection unit 40 is not required to have such a ballpoint pen type. Accordingly, the modification of the nozzle may provide a combination in which the nozzle 22 or 32 is the ballpoint pen type nozzle illustrated in FIG. 7B, and the nozzle 42 is the sharp nozzle illustrated in FIG. 7A.

The nozzle illustrated in FIG. 7C has a form of scanning the inspection region while storing the inspection liquid at a tip end part thereof. The hollow tube 80 communicates with the tip end part of the nozzle. The tip end part of the nozzle is recessed such that the hydrophobic material or the inspection liquid is configured to be able to be stored in a recess. The nozzle stores the hydrophobic material or the inspection liquid between a recess 82 at the tip end of the nozzle and the inspection region IA, and scans the inspection region IA with the hydrophobic material or the inspection liquid. When the inspection liquid is collected, the inspection liquid may be suctioned through the hollow tube 80. As described above, the nozzles 22 and 32 may be scanning type nozzles for scanning the semiconductor substrate W with the hydrophobic material or the inspection liquid.
(Modification of Hydrophobic Material)

In the above-described embodiment, a liquid-type hydrophobic material is used as the hydrophobic material. However, the hydrophobic material may be a solid.

Figures 8, 9A, 9B:
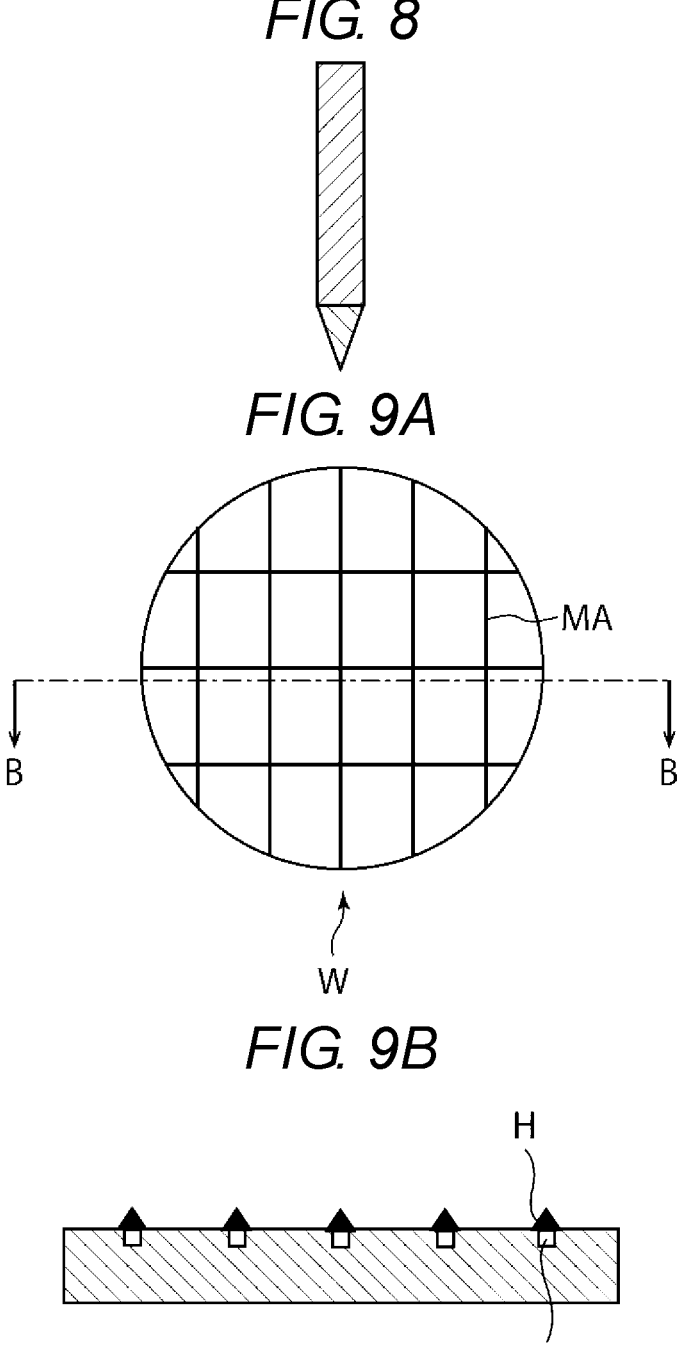
FIG. 8 is a cross-sectional view illustrating a configuration example of a nozzle in which a hydrophobic material is attached to a tip end thereof.
FIG. 9A is a plan view of a semiconductor substrate illustrating a metal analysis method according to a second embodiment.
FIG. 9B is a cross-sectional view taken along the line B-B of FIG. 9A.

FIG. 8 is a cross-sectional view illustrating a configuration example of the nozzle 22 in which the hydrophobic material is attached to the tip end thereof. When the hydrophobic material is a solid, the hydrophobic material is attached to the tip end of the nozzle 22, and the hydrophobic material is applied to the outer edge of the inspection region IA by allowing the hydrophobic material to directly contact the outer edge thereof. Here, the hydrophobic material is scraped by rubbing against the semiconductor substrate W, and the hydrophobic material remains on the semiconductor substrate W. Accordingly, the hydrophobic material can be applied to the outer edge of the inspection region IA.

When the hydrophobic material is a solid, the hydrophobic material is not required to be dried. Therefore, since the drying time Tb in FIG. 4 can be omitted, the total time Tt from the start of supplying the hydrophobic material to the end of the collection of the inspection liquid can be further shortened.

The hydrophobic material may be stuck as a hydrophobic sheet or may be sprayed with a spray.

Second Embodiment

FIG. 9A is a plan view of the semiconductor substrate W illustrating a metal analysis method according to a second embodiment. FIG. 9B is a cross-sectional view taken along the line B-B of FIG. 9A. In the second embodiment, when the semiconductor substrate W has a metal forming region MA, the hydrophobic material supply unit 20 supplies or applies the hydrophobic material H to the metal forming region MA on the semiconductor substrate W. By coating the metal forming region MA with the hydrophobic material H in advance, the metal forming region MA is hydrophobized, thereby making it possible to prevent the inspection liquid from contacting the metal forming region MA.

After the metal forming region MA is subjected to hydrophobization mask with the hydrophobic material H, the inspection liquid supply unit 30 may supply the inspection liquid to a region other than the metal formation region MA, and then the inspection liquid may be collected. Alternatively, the second embodiment may be combined with the first embodiment. For example, after the metal forming region MA is subjected to the hydrophobization mask with the hydrophobic material H, step S20 and subsequent steps in FIG. 2 maybe executed. Accordingly, after the metal forming region MA is hydrophobized, an outer edge of any inspection region can be hydrophobized to define the inspection region, and the inspection liquid can be supplied only to the inspection region. Accordingly, while the metal forming region MA is subjected to the hydrophobization mask, the inspection liquid can be supplied only to a defective location, and the inspection liquid can be collected.

According to the second embodiment, since the metal forming region MA is masked by the hydrophobic material H, it is possible to prevent metal of the metal forming region MA from being mixed into the inspection liquid. Accordingly, the inspection liquid can accurately take in a metal component such as a contaminated metal which is a target to be analyzed. As a result, the metal analyzer 1 can accurately perform the mass spectrometry on the metal component.

Figure 10:
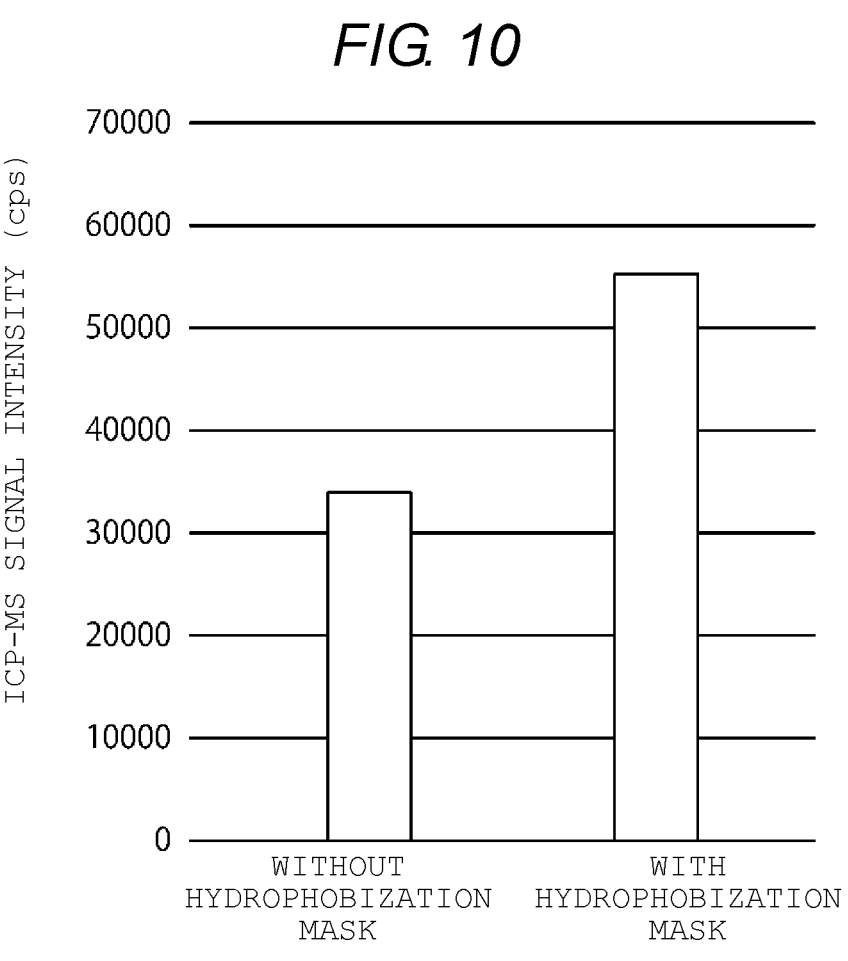
FIG. 10 is a graph illustrating ICP-MS signal intensity.

FIG. 10 is a graph illustrating an ICP-MS signal intensity. When the hydrophobization mask according to the second embodiment is not provided on the metal forming region MA, the ICP-MS signal intensity is about 33000 cps (counts per second). On the other hand, when the hydrophobization mask according to the second embodiment is provided on the metal forming region MA, the ICP-MS signal intensity is about 55000 cps. What is described above indicates that when the hydrophobization mask is provided thereon, the metal component which is the target to be analyzed significantly appears while an unnecessary interference element is not mixed into the inspection liquid, such that the sensitivity is good. Accordingly, the metal analyzer 1 according to the second embodiment can accurately perform the mass spectrometry on the metal component which is the target to be analyzed, and can prevent deterioration in quantitative properties.

(Regarding Wettability of Inspection Liquid on Semiconductor Substrate)

Figure 11A:
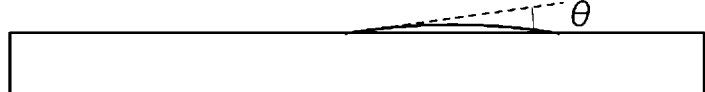
FIG. 11A is a schematic cross-sectional view illustrating wettability of the inspection liquid on the semiconductor substrate.
Figure 11B:
FIG. 11B is a schematic cross-sectional view illustrating the wettability of the inspection liquid on the semiconductor substrate.

FIGS. 11A and 11B are schematic cross-sectional views illustrating wettability of the inspection liquid on the semiconductor substrate W. FIG. 11A illustrates a state of the inspection liquid on the non-hydrophobized semiconductor substrate W. Here, a contact angle θ is significantly small, for example, 10 degrees or less. On the other hand, FIG. 11B illustrates a state of the inspection liquid on the hydrophobized semiconductor substrate W. Here, the contact angle θ becomes large, for example, 45 degrees to 60 degrees. As a result, it can be seen that an effect of the above-described embodiment can be remarkably achieved.

While certain embodiments have been described, these embodiments have been presented by way of example only, and are not intended to limit the scope of the disclosure. Indeed, the novel embodiments described herein may be embodied in a variety of other forms; furthermore, various omissions, substitutions and changes in the form of the embodiments described herein may be made without departing from the spirit of the disclosure. The accompanying claims and their equivalents are intended to cover such forms or modifications as would fall within the scope and spirit of the disclosure.

What is claimed is:

1. An analysis system, comprising:
a stage that supports a sample having a surface;
a first supplier configured to supply a hydrophobic material on the surface of the sample to form a hydrophobic material inner edge of an inspection region having a rectangular shape when viewed in a direction perpendicular to the surface of the sample to define the inspection region, the inspection region being a part of the surface of the sample;
a second supplier configured to supply an inspection liquid on the inspection region, the supplied inspection liquid being accumulated on the inspection region while being dammed up by the hydrophobic material inner edge;
a collector configured to collect the inspection liquid accumulated on the inspection region within the hydrophobic material inner edge;
an analyzer configured to analyze a component contained in the collected inspection liquid; and
wherein the first supplier supplies the hydrophobic material on a first place of the surface of the sample to form a first hydrophobic material inner edge having the rectangular shape to define a first inspection region, after supply of the hydrophobic material on the first place, the first supplier supplies the hydrophobic material on a second place of the sample to form a second hydrophobic material inner edge having the rectangular shape to define a second inspection region, the second place being different from the first place, and supply of the hydrophobic material on the second place overlaps in time with supply or collection of the inspection liquid on or from the first inspection region.

2. The analysis system according to claim 1, further comprising:
a memory that stores coordinate information of the first inspection region on the sample; and a first drive mechanism that moves the first supplier to surround the first inspection region with the hydrophobic material, based upon the coordinate information.

3. The analysis system according to claim 2, further comprising:
a second drive mechanism that moves at least one of the second supplier or the collector above the first inspection region, based upon the coordinate information.

4. The analysis system according to claim 1, wherein the second supplier and the collector share a same nozzle.

5. The analysis system according to claim 1, wherein the analyzer is configured to detect a metal component contained in the inspection liquid.

6. The analysis system according to claim 1, wherein the hydrophobic material has hydrophobicity.

7. The analysis system according to claim 1, wherein the inspection liquid includes at least one of: a liquid containing HF and $H_2O$; a liquid containing HF and $H_2O_2$; a liquid containing HF, HCl, and $H_2O_2$; or a liquid containing HF, $HNO_3$, and HCl.

8. The analysis system according to claim 1, wherein the hydrophobic material is a liquid or a solid containing 1-bromopropane ($CH_3CH_2CH_2Br$).

9. The analysis system according to claim 1, wherein a contact angle between the inspection liquid and the surface of the sample including the hydrophobic material is between about 45 degrees and about 60 degrees.

10. An analysis method using an analyzer including a stage, a first supplier configured to supply a hydrophobic material over a sample having a surface, a second supplier configured to supply an inspection liquid on the surface of the sample, a collector configured to collect the inspection liquid, and an analyzer configured to analyze a component contained in the inspection liquid, the method comprising:
placing the sample on the stage;
supplying the hydrophobic material on the surface of the sample to form a hydrophobic material inner edge of an inspection region having a rectangular shape when viewed in a direction perpendicular to the surface of the sample to define the inspection region, the inspection region being a part of the surface of the sample;
supplying the inspection liquid on the inspection region, the supplied inspection liquid being accumulated on the inspection region while being dammed up by the hydrophobic material inner edge;
collecting the inspection liquid accumulated on the inspection region within the hydrophobic material inner edge;
analyzing a component contained in the collected inspection liquid; and
wherein the hydrophobic material is supplied on a first place of the surface of the sample to form a first hydrophobic material inner edge having the rectangular shape to define a first inspection region, after supply of the hydrophobic material on the first place, the first supplier supplies the hydrophobic material on a second place of the sample to form a second hydrophobic material inner edge having the rectangular shape to define a second inspection region, the second place being different from the first place, and supply of the hydrophobic material on the second place overlaps in time with supply or collection of the inspection liquid on or from the first inspection region.

11. The analysis method according to claim 10 using the analyzer further including a first drive mechanism that moves the first supplier, and a second drive mechanism that moves at least one of the second supplier or the collector, the method further comprising:

surrounding the first inspection region with the hydrophobic material based upon coordinate information of the first inspection region on the sample, wherein the inspection liquid is supplied to the first inspection region to allow the inspection liquid to stay in the first inspection region, and the inspection liquid is not supplied to an outside of the first inspection region.

12. The analysis method according to claim 10, further comprising:

drying the hydrophobic material after the hydrophobic material is provided over the sample and before the inspection liquid is supplied.

13. The analysis method according to claim 10, wherein the component includes a metal component.

14. The analysis method according to claim 13, wherein the first inspection region includes a metal forming region of the sample.

15. The analysis method according to claim 10, wherein the hydrophobic material has hydrophobicity.

16. The analysis method according to claim 10, wherein the inspection liquid includes at least one of: a liquid containing HF and $H_2O$; a liquid containing HF and $H_2O_2$; a liquid containing HF, HCl, and $H_2O_2$; or a liquid containing HF, $HNO_3$, and HCl.

17. The analysis method according to claim 10, wherein the hydrophobic material is a liquid or a solid containing 1-bromopropane ($CH_3CH_2CH_2Br$).

18. The analysis system according to claim 1, wherein the first supplier applies the hydrophobic material to a metal forming region of the sample.

* * * * *